| United States Patent [19] | [11] Patent Number: 4,769,334 |
| Fleming | [45] Date of Patent: Sep. 6, 1988 |

[54] METHOD FOR DETECTING PROTEINS IN GELS USING RADIOACTIVE DYES

[75] Inventor: James E. Fleming, San Jose, Calif.

[73] Assignee: Linus Pauling Institute of Science and Medicine, Palo Alto, Calif.

[21] Appl. No.: 828,827

[22] Filed: Feb. 12, 1986

[51] Int. Cl.⁴ .................... G01N 23/00; G01N 33/68
[52] U.S. Cl. ............................................ 436/57; 436/86
[58] Field of Search ...................... 436/57, 86, 87, 88, 436/174–178

[56] References Cited

U.S. PATENT DOCUMENTS

| | | |
|---|---|---|
| 3,415,776 | 12/1968 | White . |
| 4,153,416 | 5/1979 | Bonner et al. ............... 436/57 |
| 4,180,513 | 12/1979 | Chiang . |
| 4,239,495 | 12/1980 | Gindler et al. ............... 436/86 |
| 4,293,436 | 10/1981 | Fost ............................. 436/57 X |
| 4,405,720 | 9/1983 | Merril .......................... 436/86 |
| 4,459,356 | 7/1984 | Gersten ........................ 436/86 |

OTHER PUBLICATIONS

Zapolski et al., Electrophoresis, vol. 5, pp. 354–357, 1984.
Zapolski et al., Anal. Biochem., vol. 123, pp. 325–328, 1982.
Kuhn et al., Anal. Biochem., vol. 105, pp. 274–280, 1980.
Means et al., Biochemistry, vol. 7, No. 6, pp. 2192–2201, 1968.
Christopher et al., Anal. Biochem., vol. 85, pp. 404–412, 1978.
Hames et al., *Gel Electrophoresis of Proteins,* IRL Press Limited, Oxford, pp. 44–46, 1981.
O'Farrell, J. Biol. Chem., vol. 250, pp. 4007–4021, 1975.
Elder et al., J. Biol. Chem., vol. 252, pp. 6510–6515, 1977.

*Primary Examiner*—Barry S. Richman
*Assistant Examiner*—Robert J. Hill, Jr.
*Attorney, Agent, or Firm*—Flehr, Hohbach, Test, Albritton & Herbert

[57] ABSTRACT

A method is provided for detecting proteins on gels utilizing $^{14}C$-labeled dyes.

6 Claims, No Drawings

METHOD FOR DETECTING PROTEINS IN GELS USING RADIOACTIVE DYES

The present invention is directed to a method for detecting proteins on gels using radioactive dyes. In particular, the invention is directed to a method for detecting proteins on gels using $^{14}$C-labeled dyes.

BACKGROUND OF THE INVENTION

There are a variety of dyes available for the detection of proteins and peptides on gels, particularly polyacrylamide gels, after the proteins or peptides have been separated by electrophoresis, chromatography, or other method. However, there is a continuing need for increasingly sensitive agents which may accurately detect presence of proteins in smaller amounts and in particular which allow quantitative determination of the protein. Thus, there is a continuing need for dyes which are accurate using diminished protein loads while retaining versatility in detecting a wide variety of proteins and peptides.

One of the more sensitive detecting methods employs the use of staining procedures based upon the precipitation of silver on the protein, the so-called silver-staining method. There are different disadvantages however with the silver-staining method, one of which being that the color of silver-stained spots may fade and/or change color with time. The silver-staining proceedure itself is rather time consuming and requires many steps. Furthermore, because the detection threshold and slope of the mass/grain intensity relationship utilizing silver stains differs for various proteins and with various silver stains, reliable results may not be consistently obtained. Probably most importantly, the silver-staining technique is not adequate for quantitative determination of the protein. See Zapolski, et al., *Electrophoresis*, 5, 354-357 (1984).

The class of dyes known as the Coomassie ® dyes, in particular Coomassie Blue R-250, although not quite as sensitive as silver stains, has been a widely used dye due to its versatility, ease of use, and its adaptability for quantitative determination of proteins. However, the usefulness of Coomassie dye is still limited by its sensitivity.

In a search for more sensitive dyes, Zapolski, et al., supra, made a variety of $^{35}$S-labeled stains for the detection of proteins on sodium dodecyl sulfate (SDS) polyacrylamide gels. However, the study was not made for quantitative use of the dyes and the authors determined that the $^{35}$S-labeled Coomassie Blue R-250 was not a promising dye for this purpose. Zapolski, et al., *Analytical Biochemistry*, 123, 325-328 (1982) also studied the $^{59}$Fe-labeled ferrous bathophenanthroline sulfonate (BPS) as a protein-staining dye. However, use for quantitative work was not determined nor was its versatility for use with a variety of proteins.

Autoradiography has also been utilized to detect proteins on gels. However, this technique requires the labeling of the proteins to be detected prior to their application onto the gel. However, many types of protein samples, cannot be readily radiolabeled, such as human proteins, and therefore are not amenable to autoradiography.

There is therefore a continuing need to develop materials for detection of proteins on gels which are improved in one or more of the following aspects: ease of use, safety in handling, sensitivity, versatility, applicability for quantitative work.

It is therefore an object of the present invention to provide an improved method for detecting proteins on gels, both in qualitative and quantitative applications, using dyes with enhanced sensitivity as well as versatility, ease and safety of use.

These and other objects will become apparent from the following description of the preferred embodiments and from the appended claims.

SUMMARY OF THE INVENTION

The present invention provides a method for detecting proteins on gels comprising the steps of contacting a protein on a gel with a $^{14}$C-labeled dye of the formula (I) or (II):

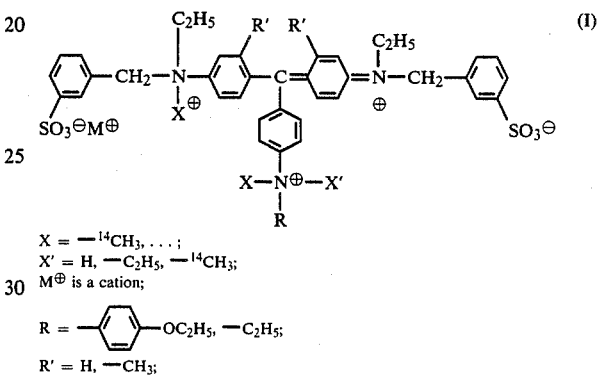

$X = -^{14}CH_3, \ldots;$
$X' = H, -C_2H_5, -^{14}CH_3;$
$M^\oplus$ is a cation;

$R = $ —⟨⟩—$OC_2H_5$, $-C_2H_5$;

$R' = H, -CH_3;$ with the provisio that at least one X or X' group is $^{14}CH_3$;

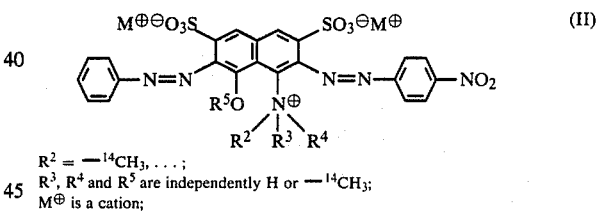

$R^2 = -^{14}CH_3, \ldots;$
$R^3, R^4$ and $R^5$ are independently H or $-^{14}CH_3$;
$M^\oplus$ is a cation;

with the proviso that at least one $R^2$, $R^3$, $R^4$, or R group is $-^{14}CH_3$ to form a dye-protein complex; and detecting the radioactive emission from the complex on the gel.

DESCRIPTION OF THE INVENTION

The present invention utilizes dyes formed by the $^{14}$C-methylation of dyes having the formulas:

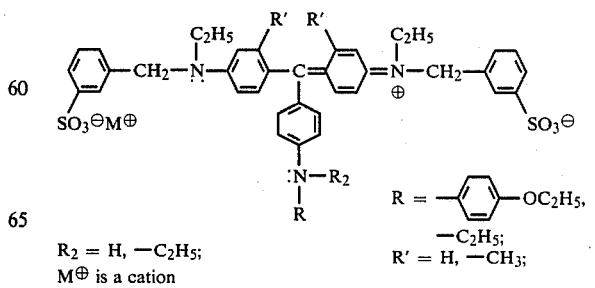

$R_2 = H, -C_2H_5;$
$M^\oplus$ is a cation $R = $ —⟨⟩—$OC_2H_5$,
$-C_2H_5;$
$R' = H, -CH_3;$

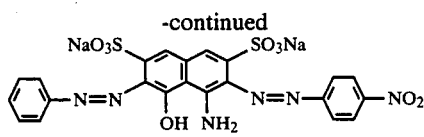

By labeling the above described dyes with a suitable $^{14}C$-methylating agent, such as $^{14}C$-formaldehyde, dyes useful in accordance with the present invention are formed characterized by the following formulas (I) and (II):

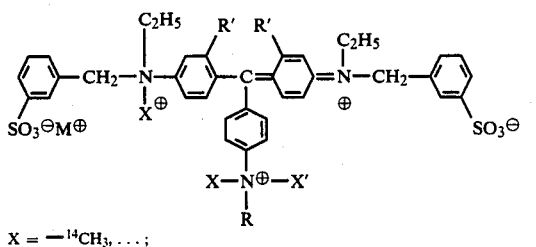

$X = -^{14}CH_3, \ldots;$
$X' = H, -C_2H_5, -^{14}CH_3;$
$M^\oplus$ is a cation;

$R = $ -⟨⟩-$OC_2H_5$, $-C_2H_5$;
$R' = H, -CH_3;$ with the proviso that at least one of the substituents X and X' is a $^{14}C$-methyl group;

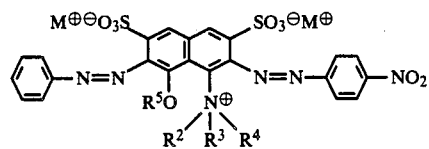

$R^2 = -^{14}CH_3, \ldots;$
$R^3, R^4$ and $R^5$ are independently H or $-^{14}CH_3$;
$M^\oplus$ is a cation;

with the proviso that at least one $R^2$, $R^3$, $R^4$, or R group is $-^{14}CH_3$.

Methods are known in the art for labeling amino groups using $^{14}C$-formaldehyde, such as that disclosed by Means and Feeney, *Biochemistry*, 7, 2192–2201 (1968); or Kuhn and Wilt, *Anal. Biochem*, 105, 274–280 (1980). Generally, the unlabeled dye will be dissolved in a suitable buffer solution, then treated with the $^{14}C$-formaldehyde, usually at room temperature. The resulting oxime is then reduced by a suitable reducing agent such as sodium borohydride to produce the $^{14}C$-methylated dye. At least one $^{14}C$-methyl group will be added to the dye, but in some instances more than one $^{14}C$-methyl group may be added.

While the above-described method of methylating the dye via the oxime will methylate primary and secondary amino groups on the dye, other methods of methylation may be used such as methylation by $^{14}C$-methyliodide, to methylate tertiary amines and to methylate primary and secondary amines up to the point of quaternary saturation. $^{14}C$-Methyliodide may also be used to methylate the hydroxy group in the dye of Formula (II). While not limiting the invention to a particular theory, it is believed that N-methylation leads to substantially monomethylation, i.e., where X' is hydrogen and X is . . . (Formula I) and $R^5$ is hydrogen and $R^2$ is . . . (Formula II).

The $^{14}C$-labeled dyes will be used in a conventional manner on gels, in particular, polyacrylamide gels of all types. Due to the enhanced ability to detect the dye-protein complexes formed according to the present invention, lower protein loadings may be used in the dye than would be conventionally used using an unlabeled dye. Furthermore, due to the enhanced ability to detect the radioactive dye, the proteins may be quantitatively analyzed using conventional $^{14}C$ detecting methods and instruments. For example, the labeled dye-protein complex may be detected using conventional fluorograms and/or beta-scanning instruments.

The amount of dye used in a particular case will depend on the thickness of the gel utilized, the separation techniques utilized to separate the proteins on the gel, the amount of protein needed to be detected and/or quantified, and the nature of the protein. The appropriate amount of radiolabeled dye to be utilized in any particular instance may be readily determined by those of ordinary skill in the art. Once the gel, protein, protein concentration range, and the like are determined, a standard curve may be first formed to correlate protein concentrations with a convenient measurable parameter using the radio emission data.

The radio emission data may be processed and correlated to quantify the amount of protein by known mathematical methods. For example, quantitation of data from fluorograms may be performed by computer-assisted microdensitometry by the methods disclosed by Latter, et al., *Electrophoresis*, 4, 122–126 (1983).

The following example is presented to help in the better understanding of the present invention and for purposes of illustration. The example, however, is not to be construed as limiting the invention to the precise form disclosed or to limit the scope of the invention in any manner or means.

EXAMPLE

All electrophoresis reagents and Coomassie ® R-250 (R'=H, R=4-ethoxy-phenyl) were obtained from Bi-oRad, Richmond, CA. [$^{14}C$]-formaldehyde (sp. Act. 52.5 mci/mmol) and Enlightening ™ were procurred from New England Nuclear and protein molecular weight markers were from Sigma Chemical Co., St. Louis, MO. The labeling of Coomassie ® R-250 was carried out as follows. Coomassie ® R-250, was dissolved in 0.25M Na borate, pH 9, at a concentration of 0.1 mg/ml. [$^{14}C$]-formaldehyde, 0.12 mCi, was added to the Coomassie solution at room temperature and after 10 seconds 1 mg $NaBH_4$ was added to the mixture. After about 10 minutes, 1 ml of 2M HCl was added to remove the unreacted borohydride. This solution was then used for the staining of proteins in SDS-polyacrylamide gels.

SDS polyacrylamide slab gel electrophoresis of six proteins was carried out with a 10% acrylamide running gel with a 3% stacking gel. After electrophoresis, the gels were incubated with shaking in the labeled Commassie solution for 18 hours. After the incubation, the gel was extensively washed in 5% acetic acid until clear backgrounds were obtained. Gels were then soaked in Enlightening ™ for 30 minutes and dried on a Hoeffer slab gel dryer model SE1150 for 60 minutes at 60° C. The dried gel was then exposed to preflashed Kodak ® XAR5 X-ray film for 1 week at −76° C. The exposed film was developed in a Kodak ® Model M5AN X-Omat processor. Quantitation of the bands on the fluorograms was performed by computer assisted microdensitometry as described by Latter, et al., supra.

The foregoing description of the preferred embodiments of the invention is presented for the purposes of illustration and description. It is not intended to be exhaustive or to limit the invention to the precise forms disclosed and obviously many modifications and variations are possible in light of the above teaching. The particular embodiments described above were chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

I claim:

1. A method for detecting a protein on a gel comprising the steps of:

contacting said protein on a gel with a $^{14}$C-labeled dye of the formula (I) or (II):

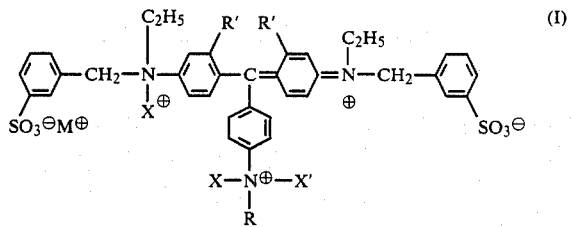

$X = -^{14}CH_3, \ldots;$
$X' = H, -C_2H_5, -^{14}CH_3;$
$M^\oplus$ is a cation;

$R = \text{—phenyl—}OC_2H_5, -C_2H_5;$
$R' = H, -CH_3;$ with the proviso that at least one X or X' group is $^{14}CH_3$;

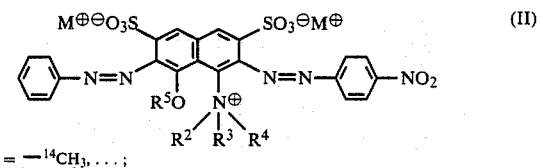

$R^2 = -^{14}CH_3, \ldots;$
$R^3, R^4$ and $R^5$ are independently H or $-^{14}CH_3;$
$M^\oplus$ is a cation;

with the proviso that at least one $R^2$, $R^3$, $R^4$, or R group is $-^{14}CH_3$ to form a dye-protein complex; and detecting the radioactive emission from said complex on said gel.

2. A method according to claim 1 further comprising the step of measuring the amount of said protein on said gel by correlating said detected radioactive emission to a predetermined standard curve.

3. A method according to claim 1 wherein said gel comprises polyacrylamide gel.

4. A method according to claim 3 wherein said dye is of the Formula II, $R^5$ is hydrogen and $R^2$ is.

5. A method according to claim 3 wherein said dye is of the Formula I and R' is hydrogen and R is 4-ethyoxyphenyl.

6. A method according to claim 5 wherein X' is hydrogen and one X is.

* * * * *